United States Patent [19]

Puscas et al.

[11] 4,221,783

[45] Sep. 9, 1980

[54] COMPOSITION AND METHOD FOR THE TREATMENT OF DUODENAL ULCERS, GASTRITIS AND GASTRO-DUODENITIS

[75] Inventors: Ioan Puscas, Simleul Silvaniei; Ioan Orban, Jud Salaj; Livia Voicu, Simleul Silvaniei; Dorin Breazu, Cluj-Napoca; Ioan Pop, Cluj-Napoca; Iuliu Ciupe, Cluj-Napoca; Lazar Terec, Gherla; Mioara R. Butan, Cluj-Napoca; Aurel Chiu, Simleul Silvaniei; Aurel Lerintiu, Simleul Silvaniei; Zoltan Turi, Simleul Silvaniei, all of Romania

[73] Assignee: Centrala Industriala de Medicamente Cosmetice Coloranti si Lacuri, Bucharest, Romania

[21] Appl. No.: 10,906

[22] Filed: Feb. 9, 1979

Related U.S. Application Data

[63] Continuation-in-part of Ser. No. 906,202, May 15, 1978, abandoned.

[30] Foreign Application Priority Data

May 14, 1977 [RO] Romania ................................. 90347
May 14, 1977 [RO] Romania ................................. 90349
May 14, 1977 [RO] Romania ................................. 90350
May 14, 1977 [RO] Romania ................................. 90351
Apr. 13, 1978 [RO] Romania ................................. 93790

[51] Int. Cl.$^2$ .................... A61K 33/00; A61K 33/10; A61K 33/08
[52] U.S. Cl. .................................. 424/127; 424/156; 424/157; 424/270
[58] Field of Search ................ 424/157, 156, 127, 270

[56] References Cited

PUBLICATIONS

The Merck Index, Ninth Ed. (1977) pp. 6, 7, 143, 494 & 778, Merck & Co., Inc., Rahway, N.J.
Handbook of Nonprescription Drugs, Fifth Ed. (1977), pp. 13–17—Amer. Pharm. Assoc.—Wash., D.C.

*Primary Examiner*—Frederick E. Waddell

[57] ABSTRACT

Gastro-duodenal ulcers, gastritis and gastro-duodenitis may be effectively treated with a composition comprising a sulfonamide having an —SO$_2$NH$_2$ group linked to a thiazolic or benzothiazolic ring together with an alkali metal bicarbonate, an alkali metal citrate, a magnesium compound and optionally aluminum hydroxide.

13 Claims, No Drawings

COMPOSITION AND METHOD FOR THE TREATMENT OF DUODENAL ULCERS, GASTRITIS AND GASTRO-DUODENITIS

This application is a continuation-in-part of copending application, Ser. No. 906,202 filed May 15, 1978 now abandoned.

This invention relates to medicinal compositions, more particularly, the present invention relates to compositions suitable for use in the treatment of gastritis; gastro-duodenitis and gastro-duodenal ulcers.

Heretofore, both medicinal techniques and surgical procedures have been commonly used in the treatment of gastro-duodenal ulcers. The medicinal methods employed typically have focused upon the pathogenetic links which intervene in ulcerogenesis and may involve neutralization of gastric acid secretion, dressings of the gastric mucous membrane, the use of substances which enhance the factors protecting the gastric mucous membrane, anticholinergics (vagolitics), tranquilizers, and the like. Medications employed for such purposes include sodium bicarbonate, compositions containing colloidal aluminum hydroxide, belladone extract, salts of calcium, magnesium, and bismuth, various silicates, scopalamine derivatives and combinations thereof with tranquilizers or flavoring substances which enhance digestion.

The surgical procedures employed for treatment of gastro-duodenal ulcers are directed to the elimination of those zones which play a role in the secretion of gastric acids. These procedures include gastric resection, antrectomy, vagatomy, and variations thereof.

Each of these noted techniques is primarily directed to precluding the formation of hydrochloric acid in the parietal cell and migration thereof to the fundic zone of the stomach. Although these medicinal and surgical techniques have been employed with varying degrees of success, research efforts have continued with the goal of developing improved medications designed to obviate the necessity of surgery.

In accordance with the present invention, this end is attained by the use of a composition which is capable of inhibiting the carbonic anydrase enzyme (carboanhydrase) which, when present in the renal tubules, erythrocytes, and other tissues, catalyzes the reversible hydration of carbon dioxide as shown by the following equation:

$$CO_2 + H_2O \rightleftharpoons H^+ + HCO_3^-$$

During the course of this reaction, the liberated hydrogen ion is replaced by the sodium ion of the tubal urine which then combines with the $HCO_3^-$ ion and reappears as sodium in extracellular fluid. The hydrogen ion is eliminated either in the form of $NH_4^+$ ions or as an acid salt such as disodium phosphate. Inhibition of enzyme formation pursuant to the invention results in diminution of carbonic acid formation as well as a lessening in the rate of formation of hydrogen ions.

The compositions described herein include a carbonic anhydrase inhibitor as an active component which comprises a sulfonamide including an $SO_2NH_2$ group linked either to a thiazolic or benzothiazolic ring together with an alkali metal bicarbonate (e.g., sodium and/or potassium), an alkali metal citrate (e.g., sodium or potassium), the oxide or carbonate of magnesium, and aluminum hydroxide.

The sulfonamides described herein are of the general formula

wherein R is selected from the group consisting of
(a) 2-acetylamino-1,3,4-thiadiazole-5-sulfonamide,
(b) 5-acetylamino-4,methyl-$\Delta^2$-1,3,4-thiadiazoline-2-sulfonamide,
(c) 6-ethoxy-2-benzothiazole-sulfonamide, and
(d) 5-benzosulfonamide-1,3,4-thiadiazole-2-sulfonamide.

The described compositions may conveniently be prepared in tablet or powder form together with adjuvants commonly employed for the rapid disintegration of tablets. The constituent, components of the described composition may be employed in amounts falling within the broad ranges set forth in the following table, the quantities being expressed in weight percentages:

TABLE

| Compound | Amount Present (weight %) |
|---|---|
| linked sulfonamide | 5–40 |
| bicarbonates of alkali metals | 15–30 |
| alkali metal citrate | 10–40 |
| magnesium compound 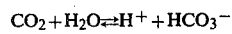 (oxide or carbonate) | 14–30 |
| aluminum hydroxide | 0–15 |

The noted compositions may be effectively employed in treating gastro-duodenal ulcers in adults and children and is particularly effective in treating cases with chronic and gigantic recesses or those evidencing an ususually high degree of gastric acid secretion. This end is attained by use of the noted sulfonamides which act to diminish gastric secretion. Electrolytic losses are compensated by means of adjuvants.

Administration of the described medication may be effected orally, after meals, with a frequency ranging from 2–4 times per day for a time period ranging from 2–5 weeks. In administering the drug, it is important to avoid exceeding the daily permissible therapeutic doses, which are determined on the basis of the body weight of the patient the doses falling within the following ranges: 200–3000 mg acetazolamide, 60–1500 mg methazolamide, 30–800 mg benzolamide, 100–3000 mg ethoxolamide, 100–3500 mg alkali metal bicarbonate, 100–4000 mg alkali metal citrate, 100–3000 mg magnesium oxide or carbonate and 50–1500 mg aluminum hydroxide. During treatment, the patient does not require a strict hygieno-dietic diet.

Several examples of medicinal compositions in accordance with the present invention are set forth below. It will be understood by those skilled in the art that these exemplary embodiments are for purposes of exposition and are not be contrued as limiting.

| Examples I and II | I % by weight | II % by weight |
|---|---|---|
| Ethoxolamide | 15.38 | 20.00 |
| Potassium bicarbonate | 23.08 | 23.33 |
| Sodium citrate | 30.77 | 26.67 |
| Magnesium oxide | 23.08 | 20.00 |
| aluminum hydroxide | 7.69 | 10.00 |

| Examples III and IV | III % by weight | IV % by weight |
|---|---|---|
| Benzolamide | 5.17 | 6.25 |
| Sodium bicarbonate | 25.86 | 27.34 |
| Potassium citrate | 34.48 | 31.25 |

-continued

| | | |
|---|---|---|
| Magnesium carbonate/oxide | 25.86 | 23.44 |
| aluminum hydroxide | 8.63 | 11.72 |

| Examples V and VI | V % by weight | VI % by weight |
|---|---|---|
| Methazolamide | 11.77 | 12.50 |
| Potassium bicarbonate | 29.41 | 29.17 |
| Sodium citrate | 39.21 | 33.33 |
| Magnesium carbonate | 19.61 | 25.00 |

| Exampls VII and VIII | VII % by weight | VIII % by weight |
|---|---|---|
| Acetazolamide | 38.30 | 36.36 |
| Potassium citrate | 21.28 | — |
| Sodium citrate | — | 13.64 |
| Sodium bicarbonate | 17.02 | 4.54 |
| Potassium bicarbonate | — | 13.64 |
| Magnesium oxide | 14.89 | 18.18 |
| Aluminum hydroxide | 8.51 | 13.64 |

| Examples IX and X | IX % by weight | X % by weight |
|---|---|---|
| Acetazolamide | 38.10 | 40.00 |
| Potassium bicarbonate | 11.43 | 14.00 |
| Sodium bicarbonate | 11.43 | 5.00 |
| Sodium citrate | 13.34 | 15.00 |
| Magnesium oxide | 19.04 | 18.00 |
| Aluminum hydroxide | 6.66 | 8.00 |

Adjuvants employed in preparing tablets of the above-described compositions may be selected from among sodium carboxymethylcellulose, polyvinyl pyrolidone, magnesium steorate, talc, and the like.

Evaluation of patients treated with compositions of the invention reveal that closure of gastric recess is effected within a time period ranging from 10–18 days, such being for superior to that attainable with known prior art medications. Furthermore, surgery was avoided in each case. Additionally, closure of recesses in a duodenal ulcer was attained in all cases within 3 to 5 days after treatment. And lastly, in peptic post-operative ulcers and pyloric stenosis, use of the described composition limited further surgical intervention.

What is claimed is:

1. Pharmaceutical composition for the treatment of gastro-duodenal ulcers, gastritis and gastro-duodenitis comprising
   (a) from 5–40%, by weight, of a sulfonamide having an —$SO_2NH_2$ group linked to a ring structure selected from the group consisting of a thiadiazolic ring and a benzothiazolic ring,
   (b) from 15–30%, by weight, of an alkali metal bicarbonate selected from the group consisting of the bicarbonates of sodium and potassium,
   (c) from 10–40%, by weight, of an alkali metal citrate selected from the group consisting of the citrates of sodium and potassium,
   (d) from 15–30%, by weight, of a magnesium compound selected from the group consisting of magnesium carbonate and magnesium oxide, and
   (e) from 0–15%, by weight, of aluminum hydroxide.

2. Pharmaceutical composition of matter for the treatment of gastro-duodenal ulcers, gastritis and gastro-duodenitis comprising
   (a) from 5–40%, by weight, of a sulfonamide derivative selected from the group consisting of ethoxzolamide, benzolamide, methazolamide and acetazolamide.
   (b) from 15–30%, by weight, of an alkali metal bicarbonate selected from the group consisting of sodium bicarbonate and potassium bicarbonate,
   (c) from 10–40%, by weight, of an alkali metal citrate selected from the group consisting of sodium citrate and potassium citrate,
   (d) from 15–30%, by weight, of a magnesium compound selected from the group consisting of magnesium oxide and magnesium carbonate, and
   (e) from 0–15%, by weight, of aluminum hydroxide.

3. Composition in accordance with claim 2 wherein said sulfonamide is ethoxzolamide.

4. Composition in accordance with claim 2 wherein said sulfonamide is benzolamide.

5. Composition in accordance with claim 2 wherein said sulfonamide is methazolamide.

6. Composition in accordance with claim 2 wherein said sulfonamide is acetazolamide.

7. Method for the treatment of gastro-duodenal ulcers, gastritis and gastro-duodenitis which comprises administering to a patient having same an effective dosage of a pharmaceutical composition comprising
   (a) from 5–40%, by weight, of a sulfonamide derivative selected from the group consisting of ethoxzolamide, benzolamide, methazolamide and acetazolamide,
   (b) from 15–30%, by weight, of an alkali metal bicarbonate selected from the group consisting of sodium bicarbonate and potassium bicarbonate,
   (c) from 10–40%, by weight, of an alkali metal citrate selected from the group consisting of sodium citrate and potassium citrate,
   (d) from 15–30%, by weight, of a magnesium compound selected from the group consisting of magnesium oxide and magnesium carbonate, and
   (e) from 0–15%, by weight, of aluminum hydroxide, said composition being administered orally, at least three times a day after meals for a time period ranging from 2–4 weeks dependent upon the diagnosis and severity of the case.

8. Method in accordance with claim 7 wherein said sulfonamide is ethoxolamide, the dosage thereof ranging from 100–3000 mg daily.

9. Method in accordance with claim 7 wherein said sulfonamide is benzolamide, the dosage thereof ranging from 30–800 mg daily.

10. Method in accordance with claim 7 wherein sulfonamide is methazolamide, the dosage thereof ranging from 60–1500 mg daily.

11. Method in accordance with claim 7 wherein said sulfonamide is acetazolamide, the dosage thereof ranging from 200–3000 mg daily.

12. Method in accordance with claim 7 wherein said pharmaceutical composition is administered in tablet form.

13. Method in accordance with claim 7 wherein said pharmaceutical composition is administered in powder form.

* * * * *